United States Patent
Rupp et al.

(10) Patent No.: US 10,843,111 B2
(45) Date of Patent: Nov. 24, 2020

(54) PROCESS OF SEPARATING BLOOD PLASMA/SERUM FROM WHOLE BLOOD

(71) Applicant: MANN+HUMMEL GmbH, Ludwigsburg (DE)

(72) Inventors: Heike Rupp, Stuttgart (DE); Steffen Schuetz, Bietigheim-Bissingen (DE); Dagmar Winkler, Filderstadt (DE)

(73) Assignee: Mann+Hummel GmbH, Ludwigsburg (DE)

( * ) Notice: Subject to any disclaimer, the term of this patent is extended or adjusted under 35 U.S.C. 154(b) by 95 days.

(21) Appl. No.: 15/827,713

(22) Filed: Nov. 30, 2017

(65) Prior Publication Data

US 2018/0078886 A1   Mar. 22, 2018

Related U.S. Application Data

(63) Continuation of application No. PCT/EP2014/066487, filed on Jul. 31, 2014.

(30) Foreign Application Priority Data

Jul. 31, 2013   (DE) .................. 10 2013 012 677

(51) Int. Cl.

| B01D 39/06 | (2006.01) |
| B01D 39/16 | (2006.01) |
| B01D 39/20 | (2006.01) |
| A61M 1/34 | (2006.01) |
| A61K 35/16 | (2015.01) |
| B01D 39/04 | (2006.01) |
| C08L 33/12 | (2006.01) |

(52) U.S. Cl.
CPC .............. *B01D 39/06* (2013.01); *A61K 35/16* (2013.01); *A61M 1/3496* (2013.01); *B01D 39/04* (2013.01); *B01D 2239/0428* (2013.01); *B01D 2239/0485* (2013.01); *B01D 2239/065* (2013.01); *B01D 2239/1233* (2013.01); *C08L 33/12* (2013.01); *C08L 2203/02* (2013.01)

(58) Field of Classification Search
None
See application file for complete search history.

(56) References Cited

U.S. PATENT DOCUMENTS

| 3,492,396 A | 1/1970 | Dalton et al. |
| 3,992,158 A | 11/1976 | Przybylowicz et al. |
| 5,139,685 A | 8/1992 | De Castro et al. |
| 5,674,394 A | 10/1997 | Whitmore |
| 5,906,742 A | 5/1999 | Wang et al. |
| 5,919,356 A | 7/1999 | Hood |
| 5,979,669 A | 11/1999 | Kitajima et al. |
| 6,045,699 A | 4/2000 | Yazawa et al. |
| 6,140,040 A | 10/2000 | Palm et al. |
| 6,170,671 B1 | 1/2001 | Kitajima et al. |
| 2003/0206828 A1 | 11/2003 | Bell |
| 2014/0116941 A1 | 5/2014 | Thorm |

FOREIGN PATENT DOCUMENTS

| DE | 3523616 A1 | 1/1987 |
| DE | 10218554 A1 | 11/2003 |
| GB | 1516698 A | 7/1978 |
| WO | 2012143894 A1 | 10/2012 |

*Primary Examiner* — Michelle F. Paguio Frising
(74) *Attorney, Agent, or Firm* — James Hasselbeck

(57) ABSTRACT

The invention relates to whole blood filter media and a process of filtering whole blood samples using a filter medium comprising particles, wherein the blood cells are retained inside the filter, and wherein the plasma or serum is separated from the blood cells.

26 Claims, 1 Drawing Sheet

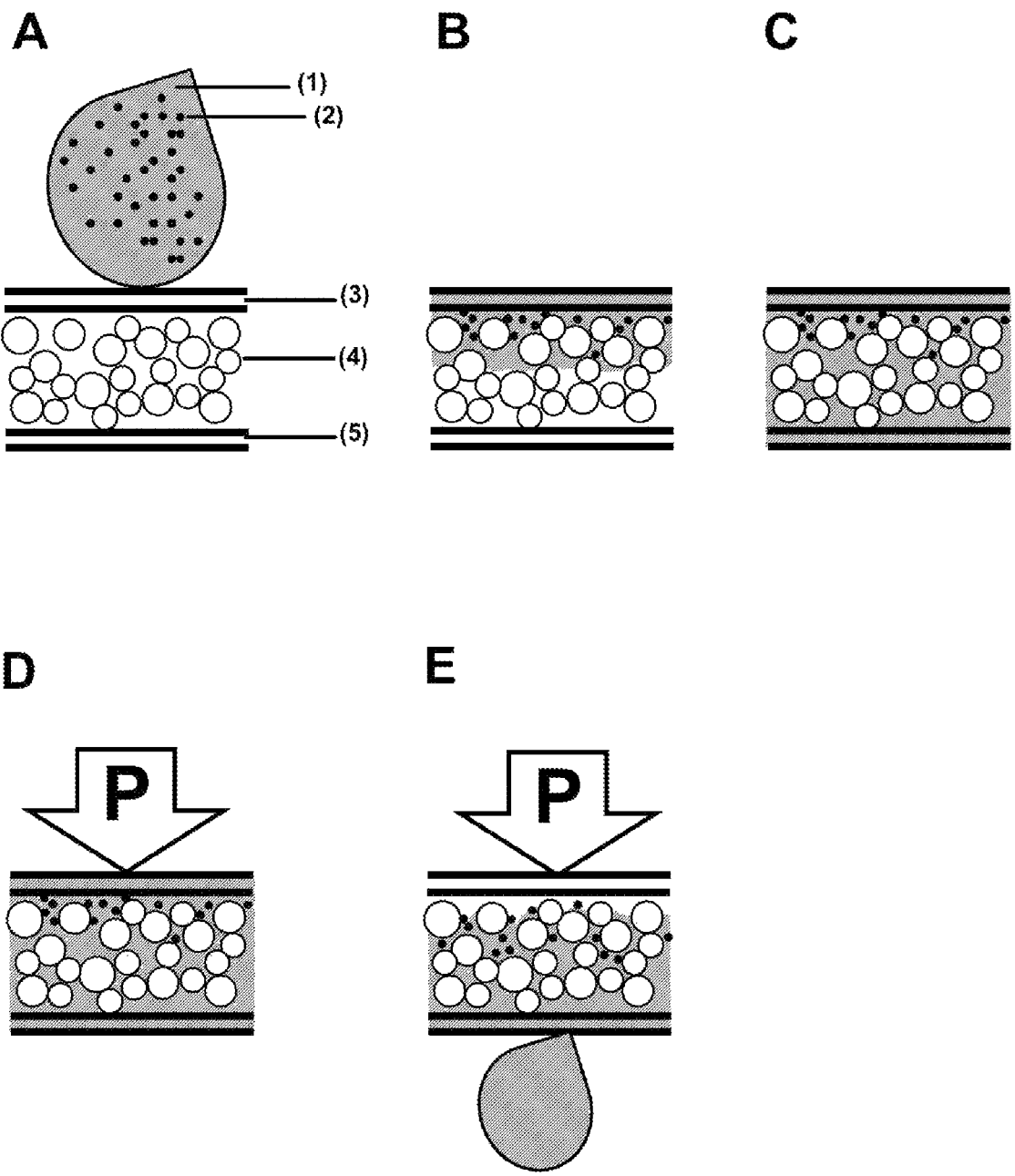

ns with each other, an outlet, and a filtration membrane selectively permeable to blood plasma separating the inlet from the outlet. Manually operable, single use pumps are connected to the inlets. A flow path is defined along the membrane between the pumps, whereby whole blood can be repeatedly exchanged between the two pumps, pass the membrane, to cause plasma to flow through the membrane and out of the outlet.
PROCESS OF SEPARATING BLOOD PLASMA/SERUM FROM WHOLE BLOOD

FIELD OF INVENTION

The present invention relates to whole blood filter media and a process of filtering whole blood, wherein the blood cells are retained in a filter comprising a bed of particles, preferably beads.

BACKGROUND OF THE INVENTION

In medical technology, various kinds of blood and plasma/serum separation and treatment processes are known and state-of-the-art. The most common method to separate blood cells from the liquid part of the blood is centrifugation.

In transfusion medicine, filters are used to remove leucocytes from transfusion blood and to remove blood clots and particles. Furthermore, artery filters are applied during surgeries, e.g. to remove blood clots, particles and gas bubbles. Plasmapheresis filters are used to clean or to substitute plasma from patients, which is poisoned by bacteria, viruses or further components, which are dangerous to life, with artificial blood plasma or plasma from donators.

Moreover, microdevices are known for whole blood analysis, which are based either on test stripes or on lab-on-a-chip technology. When using these devices, only a few microliters of blood are required for the blood or plasma/serum analysis. The separation of plasma/serum from whole blood is usually performed by fluid mechanical effects like the wetting behavior of different surfaces or the application of microchannels. Although this method is very attractive concerning the quick obtainment of blood analysis results, the results from these analyses are restricted to a few, test specific components. These applications are unable to replace a plasma/serum based blood analysis with the existing sophisticated systems in labs and hospitals, which comprise the analysis of a plurality of blood components and which are able to give an overall picture of a patient's state of health. Furthermore, also for microdevices, the task of separating blood cells from the liquid part of the blood is still not solved satisfactorily.

In many countries, it is obligatory to withdraw a sufficient amount of blood from the patients to be able to store the obtained plasma/serum sample for some time to check the analysis result some time later with a so-called retain sample. Until now, the task to obtain enough cell-free plasma/serum can however only be accomplished by centrifugation.

The centrifugation procedures, which are typically used for separating blood plasma/serum from whole blood, are not only cumbersome requiring large amounts of manual and mechanical handling, but are also time consuming, which is particularly disadvantageous in emergency medicine.

U.S. Pat. No. 5,674,394 discloses a small-volume disposable filtration technology to separate blood plasma from whole blood. The system for preparing said plasma comprises a single use filter unit having two inlets in fluid communication with each other, an outlet, and a filtration membrane selectively permeable to blood plasma separating the inlet from the outlet. Manually operable, single use pumps are connected to the inlets. A flow path is defined along the membrane between the pumps, whereby whole blood can be repeatedly exchanged between the two pumps, pass the membrane, to cause plasma to flow through the membrane and out of the outlet.

U.S. Pat. No. 5,919,356 relates to a fluid sampling device.
US2003/0206828 describes a whole blood sampling device.
U.S. Pat. No. 5,906,742 A is directed to microfiltration membranes having high pore density and mixed isotropic and anisotropic structure.
WO2012/143894 A1 relates to a method and device for the determination of analytes in whole blood.
WO93/19831 relates to a blood separation filter assembly and corresponding methods.

SUMMARY OF THE INVENTION

Blood plasma/serum analysers, which have a great capacity for plasma/serum samples, cannot operate at full capacity, if a centrifugation process is applied upstream, which works batch-wise and represents the »bottleneck« in the blood sample processing. This bottleneck problem could possibly be overcome with a filtration process instead of a centrifugation process for plasma/serum generation. Such a system would allow a flexible analysis of the samples: Urgent samples from emergency patients could be processed with a higher priority without any need of interrupting a running centrifugation process or of waiting for the centrifugation process to be finished.

It is a further advantage of a simple filtration process for whole blood separation that the whole blood separation into plasma/serum and blood cells can be performed directly after collecting the whole blood sample. This is especially advantageous for the quality of the subsequent blood analysis as the red blood cell stability decreases with increasing sample storage time. This can influence the plasma/serum composition when the plasma/serum separation is not performed immediately after the blood sample withdrawal, but with some time delay. This aspect becomes important in rural areas or developing countries when there is no centrifuge available for the plasma/serum separation and when the blood sample has to be transported for a long period of time and/or distance, sometimes even in a hot and/or humid environment.

A subsequent whole blood separation into plasma/serum can be advantageous for Point-of-Care testing devices, which are used to provide a quick blood analysis at/near the patient to get a quick blood analysis result outside of a clinical laboratory to make immediate decisions about patient care. Typically Point-of-Care testing is performed by non-laboratory personnel. A quick foregoing plasma filtration process facilitates the quick blood analysis and enables new operating conditions for Point-of-Care devices, since most of them work with whole blood or with the aforementioned microdevices which lead to a very small yield of plasma/serum volume. The whole blood separation process can also be integrated within the Point-of-Care device.

Therefore, whole blood filtration methods have been developed as an alternative measure for obtaining blood plasma/serum from whole blood. These plasma/serum filtration methods known in the art are however problematic in view of e.g. the blood cell concentration, the plasma/serum yield, the molecular adsorbance capacity, the extent of hemolysis, and the leakage of blood cells (erythrocytes, thrombocytes and leukocytes). Hemolysis is one of the important problems because the red blood cells, if ruptured, will alter the concentration of some plasma/serum analytes required for further testing and, in some cases, make an analysis using optical measurements techniques impossible due to the red color of the released hemoglobin. Moreover, the leakage of blood cells is problematic because the cells or even other particles can damage the blood plasma/serum analyzers as the sensitive capillaries and conduits can become plugged. Only (substantially) cell- and hemolysis-free plasma/serum can be used for a reliable blood analysis.

A need remains for filter media for separating blood plasma/serum from whole blood, which allow for an effective separation of blood plasma/serum from whole blood and which are suitable for use in a quick, safe and robust way to get a suitable amount of cell-free plasma/serum, without causing hemolysis. With this kind of filtration process a deterioration of the blood quality after the blood withdrawal from the patient or bad analysis results due to a time delay in a centrifugation process or due to transportation will be avoided as the blood cell separation can be performed immediately without a centrifuge in an emergency case or at the point of collection of the blood sample.

It is therefore an object of the present invention to provide a whole blood filter medium and a process for separating blood plasma/serum from whole blood, which are advantageous over the prior art, in particular regarding the problems of hemolysis and leakage of blood cells (erythrocytes, thrombocytes and leukocytes).

It is another object of the present invention to provide a whole blood filter medium and a process for separating blood plasma/serum from whole blood, wherein the separation of a sufficient amount of cell-free blood plasma/serum is possible with no or substantially no hemolysis.

It is yet another object of the present invention to provide a whole blood filter medium and a process for separating blood plasma/serum from whole blood, wherein the separation of blood plasma/serum is possible, preferably in a manual way or in an easy automatic way without using centrifugation means.

It is another object of the present invention to provide a whole blood filter medium and a process for separating blood plasma/serum from whole blood, wherein the separation is less time consuming than the separation with conventional methods such as centrifugation methods.

It should be noted in this regard that there is typically no need that the blood cells are recovered so that the process would require the step of isolating the blood cells from the filter.

It is another object of the present invention to provide a whole blood filter medium and a process for separating blood plasma/serum from whole blood from a whole blood sample in an emergency case. Ideally, the cell separation can already take place at the scene of blood withdrawal. Subsequently the obtained plasma/serum sample can be immediately processed and can be directly delivered into the blood plasma/serum analyzer, e.g. a Point-of-Care testing device. The term emergency case comprises not only patient diagnosis from accidents, but also all blood treatment processes as they are provided from medical offices or patient control during surgeries in hospitals. In this regard, it is also an object to overcome the bottleneck problem of centrifugation and/or to avoid a falsification of the blood analysis due to a long treatment or transport of the unseparated whole blood sample.

It is another object of the present invention to provide a whole blood filter medium and a process for separating blood plasma/serum from whole blood, which reduces the risk of a leakage of red blood cells into the filtrate.

It is another object of the present invention to provide a whole blood filter medium and a process for separating blood plasma or blood serum from whole blood, which leads to a cell-free or substantially cell-free plasma/serum as a filtrate, wherein the relative amounts of the molecular components to be analyzed remain substantially unchanged upon filtration. Ideally, the process comprises a filter medium that is inert and hemocompatible, releases no extractables or particles, and neither leads to the adsorption of particular blood plasma/serum components on its solid surface nor to a cross-reaction of particular blood plasma/serum components with its solid surface.

It is another object of the present invention to provide a whole blood filter medium, which can be used for separating blood plasma/serum from a whole blood sample, wherein the whole blood filter medium does not induce rupture of blood cells e.g due to frictional forces or other mechanical stresses.

It is another object of the present invention to provide a whole blood filter medium, which can be used for separating blood plasma/serum from a whole blood sample without clogging of the filter medium.

The above mentioned objects of the present invention are achieved by a whole blood filter medium and a process of filtering a sample of whole blood through a filter medium comprising a filter bed of particles, preferably beads, wherein blood cells, i.e. erythrocytes, thrombocytes and leukocytes, are retained inside the filter medium and thereby separated from the plasma/serum filtrate.

The present invention is directed to whole blood filter media and filtration processes that comprise at least a first material selected from the group consisting of glass particles, ceramic particles, mineral particles or polymer particles. The particles of the first material are preferably beads. The particles may be defined by parameters known to the skilled person such as the distribution of particle sizes as determined by the diameter, surface area, sphericity and the like.

In a preferred embodiment the filter medium comprises a bed of beads. A homogenous distribution of whole blood over the filter medium is also preferred to prevent clogging of the filter and formation of channels and short circuits. Thus, the process according to the present invention may provide the whole blood filtration of larger sample volumes than methods using membrane-based microfilter devices, such as the rapid plasma separation device of Mdi.

Moreover, the filter medium used in the process according to the present invention may further comprise a membrane located downstream of the first material. In another preferred embodiment the filter medium further comprises additionally a mesh which assists in ensuring that the blood cells are retained in the bed of the filter medium while the blood plasma/serum can pass through. In one embodiment the membrane prevents that blood cells or filter medium beads or granulate from passing into the filtrate and it therefore may enhance the yield and purity of filtrate. In another embodiment, a mesh stabilizes the filter medium and thus further prevents a deformation of the filter material, e.g. a deformation of the membrane. In addition, the whole blood filter medium of the present invention may further comprise a fiber filter layer, a foam or a sponge or a combination thereof located upstream of the first material which supports the homogeneous or substantially homogeneous distribution of whole blood over the filter surface area.

FIG. 1 illustrates a preferred example process according to the present invention. The whole blood consisting of blood cells (2) and soluble components (1) is applied to a filter medium comprising a bed of beads (4), an upstream layer, e.g. a filter fiber layer or a sponge (3) and a downstream layer, e.g. a membrane and/or a mesh (5) in step (A). The whole blood is then homogenously or substantially homogeneously distributed over the surface of the filter (B).

Optionally, pressure is applied to let the whole blood contact the filter bed. The plasma moves faster through the bed than the blood cells during wetting of the bed (C). As the bed is fully or substantially fully wetted by the plasma, pressure is optionally applied (D) and the plasma/serum filtrate is released from the filter and the blood cells remain inside the filter (E).

BRIEF DESCRIPTION OF FIGURES

FIG. 1: overview of process of separating blood plasma/serum from whole blood according to the present invention.

DETAILED DESCRIPTION OF INVENTION

As used herein, the term "whole blood" refers to blood composed of blood plasma, which is typically unclotted, and cellular components. The plasma represents about 50% to about 60% of the volume, and cellular components, i.e. erythrocytes (red blood cells, or RBCs), leucocytes (white blood cells, or WBCs), and thrombocytes (platelets), represent about 40% to about 50% of the volume. As used herein, the term "whole blood" may refer to whole blood of an animal, but preferably to whole blood of a human subject.

Erythrocytes, which contribute with about 90% to about 99% to the total number of all blood cells, have the form of biconcave discs and measure about 7 μm in diameter with a thickness of about 2 μm in an undeformed state. During maturation in the bone marrow the erythrocytes lose their nucleus. They contain the plasma membrane protein spectrin and other proteins to provide flexibility to change shape as necessary. Their unique and flexible shape enables them to pass through very narrow capillaries and provides for maximum surface area to transfer oxygen and carbon dioxide. This flexibility makes it particularly difficult to separate the red blood cells from a whole blood sample by filtration as they can elongate themselves and reduce their diameter down to about 1.5 μm. Normal whole blood has approximately 4.5 to 5.5 million erythrocytes per microliter. The life-span of erythrocytes is approximately 120 days in the circulating bloodstream. One core component of erythrocytes is hemoglobin which binds oxygen for transport to the tissues, then releases oxygen and binds carbon dioxide to be delivered to the lungs as waste product. Hemoglobin is responsible for the red color of the erythrocytes and therefore of the blood in total. Erythrocytes are the major factor contributing to blood viscosity.

Leucocytes make up less than about 1% of the total number of all blood cells and can be differentiated into different white blood cell groups (lymphocytes, granulocytes and monocytes). They can leave capillaries via diapedesis. Furthermore, they can move through tissue spaces by amoeboid motion and positive chemotaxis. They have a diameter of about 6 to about 20 μm. Leucocytes participate in the body's defense mechanisms e.g. against bacterial or viral invasion.

Thrombocytes are the smallest blood cells with a length of about 2 to about 4 μm and a thickness of about 0.9 to about 1.3 μm. They are membrane-bound cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50 to about 60 vol.-%). Plasma is devoid of cells, and unlike serum, has not clotted. So it contains all coagulation factors, in particular fibrinogen. It is a clear yellowish liquid comprising about 90 to about 95 vol.-% water.

The term "blood serum" or "serum" refers to the clear liquid that separates from blood when it is allowed to clot completely, and is therefore blood plasma from which in particular fibrinogen has been removed during clotting. Like plasma, serum is light yellow in color.

Molecular plasma or serum components can be classified into different groups including electrolytes, lipid metabolism substances, markers, e.g. for infections or tumors, enzymes, substrates, proteins and even pharmaceuticals and vitamins.

As used herein, the term "cell-free" describes a plasma/serum sample with no or substantially no cells (erythrocytes, leucocytes, thrombocytes) in its volume that is prepared by e.g. a centrifuge. A substantially cell-free or cell-free sample is needed for a subsequent plasma/serum analysis to prevent blocking of the analysis system.

For the plasma analysis performed with the plasma, which is obtained by filtration, the following analytes may be chosen which comprise the relevant molecular groups. The reference concentration ranges of these chosen analytes for whole blood with heparin stabilization depend on the applied measurement technique. The following exemplary reference concentration ranges of these chosen analytes are obtained by the analysis device "Dimension" from Siemens.

| Plasma components | | Reference concentration ranges of analytes for whole blood with heparin stabilization and the chosen measurement device |
|---|---|---|
| Electrolytes | Potassium | 3.5-5.1 mmol/l |
| | Sodium | 136-145 mmol/l |
| | Calcium | 2.12-2.52 mmol/l |
| | Magnesium | 0.74-0.99 mmol/l |
| | Chloride | 98-107 mmol/l |
| | Phosphate | 0.80-1.60 mmol/l |
| Lipids | Triglycerides | 75-175 mg/dl |
| | Cholesterol | 110-200 mg/dl |
| | HDL-cholesterol | 35-60 mg/dl |
| | LDL-cholesterol | <150 mg/dl |
| Infection markers | CRP | 0-5.00 mg/l |
| Enzymes | AST/GOT | 0-35 Unit/l |
| | Lipase | 114-286 Unit/l |
| Substrates | Albumin | 3.4-5.0 g/dl |
| | Bilirubin | 0-1.0 mg/dl |
| | Glucose | 74-106 mg/dl |
| | Creatinine | 0.60-1.30 mg/dl |
| Proteins | IgG | 6.81-16.48 g/l |
| | Ferritine | 3.0-244 ng/l |
| Hormones | TSH basal | 0.36-16.00 mUnit/l |

The analysis device "Dimension" from Siemens may not only be used for the analysis of blood plasma, but also for the analysis of blood serum.

As used herein, the expression "ensuring permeability", for example "to blood plasma or serum" or "to whole blood", preferably means that none of the above components is retained completely upon filtration. Preferably, the concentrations of the blood components are not significantly changed compared to the whole blood sample before filtration. More preferably, the concentrations of the plasma or serum components are changed by not more than about 50%, preferably by not more than about 35%, more preferably by not more than about 10%, most preferably by not more than about 8%.

As used herein, the term "hemolysis" refers to the rupture of erythrocytes, e.g. due to chemical, thermal or mechanical influences, causing the release of the hemoglobin and other internal components into the surrounding fluid. Hemolysis can be visually detected by showing a pink to red tinge in the plasma/serum. Hemolysis is a common occurrence seen in serum and plasma samples and may compromise the laboratory's test parameters for blood analysis. Hemolysis can occur from two sources. In vivo hemolysis may be due to pathological conditions such as autoimmune hemolytic anemia or transfusion reaction. In vitro hemolysis may be due to improper specimen sample collection, specimen sample processing or specimen sample transport. In particular, hemolysis may be caused by a high pressure drop and high shear or elongation rate, which may e.g. occur during filtration processes, when the sample is passed through a porous filter medium. Other important factors for hemolysis are bacterial contamination, pressure, temperature, osmotic environment, pH value, contact with surfaces, frictional forces, blood age and storage time of the unseparated whole blood sample.

The degree of hemolysis can be detected visually in comparison to a plasma reference solution having a certain concentration of hemoglobin (Hb, Hgb). Blood plasma samples having the same color as a reference solution comprising no hemoglobin show no hemolysis. Blood plasma samples being equally or less red than a solution comprising about 50 mg/dl hemoglobin show substantially no hemolysis. In this respect, "substantially no hemolysis" means that the blood plasma samples show such a degree of hemolysis that is still sufficiently low to ensure that the samples can be analyzed with satisfactory results, e.g. by the plasma analysis device "Dimension" from Siemens. Blood plasma samples being equally or less red than a solution comprising about 100 mg/dl hemoglobin show a medium degree of hemolysis. Blood plasma samples with a color corresponding to a solution with a higher hemoglobin content than 100 mg/dl show a high degree of hemolysis.

Any medium or material which shows no interaction with whole blood is generally described as "hemocompatible". No interaction means especially that the medium or material does not cause blood clotting, e.g. by interacting with the blood coagulation system or the blood platelets. Accordingly, a hemocompatible material has no thrombotic effect. It is preferred that the bulk filter media according to the present invention are hemocompatible. Furthermore, it is preferred that the filter media do not modify any blood component concentrations by adsorption or reaction and that the contact with whole blood does not cause hemolysis.

The term "diagnostic marker" as used herein refers to a molecular parameter, wherein its presence can be measured in whole blood, or preferably in blood plasma, serum, or a dilution thereof. A diagnostic marker can preferably also be quantified, and it reflects the severity or presence of a physiological state or other disease state. Further, a diagnostic marker may even indicate a risk or progression of a disease, or the susceptibility of the disease to a given treatment. Diagnostic markers can be categorized in different groups, e.g.

(a) according to their molecular structure, diagnostic markers may belong to the group comprising atomic ions, lipids, lipoproteins, steroids, sugars, nucleic acids, proteins, peptides, amino acids, alcohols and porphyrins;

(b) according to their function, diagnostic markers may belong to the group comprising electrolytes, enzymes, substrates, antibodies, hormones, toxins, neurotransmitters, drugs, metabolites, lipid metabolites, transport proteins, vitamins, or (c) according to their molecular weight; diagnostic markers may belong to the group comprising small molecule analytes of a molecular weight between 10 and 2000 Da or large molecules, which comprise proteins and protein complexes with a molecular weight higher than 2000 Da; or (d) according to their application in the detection of a specific disease; diagnostic markers may belong to the group comprising cancer markers, cardiac markers, autoimmune markers, metabolic markers.

Examples of diagnostic markers comprise potassium cation, sodium cation, calcium cation, magnesium cation, chloride, phosphate, triglycerides, cholesterol, high density lipoprotein (HDL)-cholesterol, low density lipoprotein (LDL)-cholesterol, C-reactive protein (CRP), aspartate transaminase/glutamic-oxaloacetic transaminase (AST/GOT), lipase, albumin, bilirubin, glucose, creatinine, IgG, ferritine, TSH, insulin, rheumatoid factors, prostate-specific antigen (PSA), S100B, cytochrome C, creatine kinase or troponin.

The term "capillary effects" refers to the flow of a liquid in narrow spaces without the assistance of an external force like gravity or pressure. It is based on intermolecular forces between the liquid and solid surrounding surfaces, wherein the combination of wettability, surface tension and adhesive forces between the liquid and surrounding material act to move the liquid.

The term "hydrophilic" refers to a surface, which leads to a water or blood droplet contact angle smaller than 90°, "hydrophobic" surfaces lead to a water or blood droplet contact angle bigger than 90°.

The term "sponge" refers preferably to a porous material, which can be used to soak up fluids and wherein the fluid is distributed within the sponge material. Preferably, the sponges comprise cellulose wood fibers or foamed plastic polymers or combinations thereof. In case foamed plastic polymers are applied, the plastic polymer may be selected from the group consisting of low-density polyether, polyvinylalcohol, polyurethane or polyester or a combination thereof. The sponges can be hydrophilic or hydrophobic. Preferably, the sponges are compressible. Preferably, sponges that are used upstream of the at least first material according to the process and whole blood filter medium of the present invention are hydrophobic and non-swelling (i.e. do not increase in volume upon contact with a fluid, e.g. no increase in volume of more than 10%) and preferably assist in the homogenous distribution of the whole blood over the surface of the filter bed and optionally also assist in the compression of the filter bed.

Sponges that are used downstream of the at least first material of filter medium according to the present invention are preferably hydrophilic and/or swelling, and the filtrate, which has been taken up, can be isolated, e.g. by wringing the sponge.

The term "particles" refers to small objects to which can be ascribed several physical properties such as volume or mass. As used herein, particles have the form of beads, spheres, granulate or other geometrical forms.

The term "bead" refers to a geometrical three-dimensional space with rounded edges, especially to ellipsoidal or lens-shaped geometrical three-dimensional spaces. The beads according to the present invention can be hollow or completely solid. Preferably, the beads are made of glass, polymer, ceramics or minerals. Furthermore, the beads may be coated with a hydrophilic or hydrophobic coating. In this context, the term "diameter" refers to the maximal straight distance through the bead. In this context, the term "sphericity" refers to a measure of the "roundness" of the bead. A bead with a sphericity of 1 refers to a perfectly spherical particle, while particles with a sphericity of less than 1 do not provide a perfectly spherical geometry. The sphericity can be calculated according to Wadell by the equation $$\Psi = \frac{\pi^{\frac{1}{3}}(6V_p)^{\frac{2}{3}}}{A_p},$$

wherein $V_p$ is the volume of the particle and $A_p$ is the surface area of the particle.

The sphericity of small particles can for example be determined by first determining the total volume of a bed of particles, e.g. using a pycnometer. The total surface area can then be determined by the Brunauer Teller Emmett (BET) method and the sphericity can then be calculated from these parameters. In this context, $V_p$ and $A_p$ are the total volume and the total surface area of all particles within the bed and represent the average sphericity of particles within the bed.

Preferably the beads have a sphericity higher than 0.7, more preferably higher than 0.90 and even more preferably higher than 0.95. It is particularly preferred that the beads have a sphericity of more than 0.99.

As used herein, the term "bed" or "filter bed" refers to a filter medium that comprises a volume of particles that represent the bulk of the bed. The bed is optionally compressed, e.g. by an elastic solid material e.g. by a foam or a sponge material in that way that it is included on the top of the packed bed and within the cover of the filter module top housing The purpose of this optional compression is to avoid demixing of particles with different diameters within a single filter layer and to avoid a mixing in the case of using two or more different filter layers. A fluid is applied to the raw side and moves through the filter bed and large components are retained in the filter as they may not easily pass through the space between the particles, while small components can easily bypass the particles of the bed. The particles of the bed may all have the same size or the particles may have different sizes, preferably with a specific size distribution. Preferably, the bed is a volume of first material particles in the range between 10 microliter to 10 ml, preferably between 1 ml and 2 ml.

The term "swell" or "swelling" refers to an increase of a material in volume upon contact with a fluid. Preferably, the term relates to the increase in size of more than 100%, preferably more than 50% and even more preferably more than 25%.

The expression "fiber filter layer" refers to a filter layer comprising fibers. The filter fiber layer may be woven or non-woven. The fibers may be polymer or non-polymer fibers. Preferably the polymer fibers may comprise polyester, polypropylene, polyethylene terephthalate or a combination thereof.

The term "foam" as used herein refers to a material with open pores that is formed by trapping gas in a liquid or solid.

The term "membrane" as used herein refers to a microporous structure which is a layer or film with a pore size ranging from between 0.01 μm and 25 μm, preferably between 0.1 μm and 10 μm and a thickness of less than 1 mm and preferably a thickness of less than 250 μm. Preferably, the membrane is a hydrophilic membrane and/or hemocompatible. The pore size can be determined by different methods, depending on the actual size of the pore. Suitable methods include sieving of particles with a known size or capillary flow porometry. Very small pores, in the range between 10 nm and 500 nm can for example be determined by porometry or using the retention of dextrane molecules with a known size.

The term "membrane deformation" or "deformation of the membrane" refers to the state of the membrane, wherein the shape of the membrane has been altered, typically by the application of a force such as pressure. A membrane deformation may comprise tearing the membrane, stretching of the membrane or shrinking of the membrane.

The term "mesh" as used herein refers to a solid medium, preferably a filter medium which is preferably flat and preferably produced of polymeric or metal fibers which are combined geometrically as e.g. square mesh, reverse plain Dutch weave, single plain Dutch weave or Dutch twilled weave by textile weaving technologies. Preferably, the mesh does not contribute to the separation of plasma/serum from whole blood and preferably provides a stabilizing effect and thereby counteracts the deformation of the membrane and a potential swelling of the filter bed. Preferably, the mesh provides a mesh opening between 50 μm and 1000 μm, preferably between 150 μm and 400 μm, and even more preferably between 200 and 350 μm. Preferably, the mesh is made of hydrophobic fibers or with fibers that are coated with a hydrophobic coating.

As used herein the "raw side" or "upstream" side of a filter is the side or surface through which the fluid enters the filter medium. It is considered as the entering side or surface. The "clean side" or "downstream" side of a filter is the side or surface through which the fluid exits the filter medium. It is also considered as the exiting side or surface.

As used herein the term "substantially homogeneously distributed" refers to a distribution of the whole blood on the substrate, wherein at least 90% of the surface of the substrate is covered, preferably evenly covered by the sample, preferably at least 95% of the surface is covered by the sample, and more preferably at least 98% of the surface is covered. The term "homogeneously" distributed means that at least 99% of the surface of the subject is covered by the sample.

As used herein, the term "granulate" refers to particles that are more coarse compared to the particles of the first material. The granulate may comprise glass particles or polymer particles, ceramic particles and mineral particles. Typically, the granulate particles have a lower sphericity than the beads of the first material such as below 0.7. However, granulate particles may also be beads, wherein the beads have a diameter of at least 150 μm.

As used herein, the term "wetted" refers to a surface state of the used bead or granulate particles when a thin liquid film adheres to the particles' surface. Preferably this wetting liquid film has a thickness of less than 20 micrometers. This wetting liquid film can be static or quasi-dynamic. The dynamic state is preferably given when the particles are overflown by a liquid fluid and the fluid molecules adhering to the particles' surface are replaced by other fluid molecules on a molecular scale during the flow process.

In a first embodiment, the present invention is directed to a process for filtering whole blood for separating plasma/serum from blood cells, wherein the filter comprises a filter medium comprising at least a first material selected from the group consisting of (a) glass particles,
    (b) polymer particles,
    (c) ceramic particles,
    (d) mineral particles, and
    (e) combinations thereof;
comprising the following steps:

(i) applying a whole blood sample on the raw side of the filter, (ii) optional application of positive or negative pressure, and (iii) collection of the blood plasma/serum on the clean side of the filter.

In a preferred embodiment of the process, the whole blood sample in step (i) is applied on the raw side of the filter and homogenously or substantially homogenously distributed over the raw side of the filter.

In one embodiment of the process, the pressure is applied in step (ii)

aa) after the application of the whole blood sample to the filter medium and the whole blood is in contact with the at least first material and/or bb) after the filter bed is fully wetted or substantially fully wetted.

In another embodiment, the pressure applied in step (ii) is between 0 and 1 bar, preferably between 0 and 0.5 bar, more preferably between 0 and 0.3 bar, most preferably between 0 and 0.2 bar. The pressure can either be positive pressure or negative pressure. In a preferred embodiment, the pressure is a positive pressure.

In another embodiment of the process, the filtrate is collected downstream by a sponge in step (iii) and the plasma/serum is isolated from the sponge. In one embodiment, the sponge is a hydrophilic sponge. The sponge is preferably a swelling sponge and even more preferably, the sponge provides a thickness of about 0.5 to about 8 mm. The plasma/serum may be isolated from the sponge by wringing over a filtrate collector.

In another preferred embodiment of the process, the filtrate is collected in step (iii) as drops from the downstream side of the whole blood filter medium e.g. by collection directly in a filtrate collector.

In yet another preferred embodiment, the whole blood filter medium comprises a bed of first material particles, preferably glass particles. In one embodiment, the glass particles are not coated. In another embodiment, the glass particles are coated. In another embodiment, a mixture of coated and uncoated glass particles is used. In this context, it has to be noted that the coating may slightly change the diameter and thus the size of particles compared to the uncoated particles. As used herein, the diameter of particles typically refers to the particles not including the coating. Preferably the particle is a bead.

Alternatively, in another preferred embodiment, a fraction of the glass particles between 0 wt-% and 100 wt-%, preferably between 0 wt-% and 75 wt-%, more preferably between 0 wt-% and 50 wt-% and even more preferably between 0 wt-% and 40 wt-% can be coated. Preferably the coating of the glass particles is a hydrophobic coating. In another embodiment, the coating increases the yield of the plasma and reduces the amount of plasma stuck in the filter bed.

The glass particles may be coated with suitable materials such as a polymer coating. In a preferred embodiment, the coating is a hydrophobic coating. Suitable hydrophobic coating materials are, for example, inorganic silanes or organic silanes or combinations thereof.

Preferred embodiments of the process comprise glass particles comprising borosilicate glass, soda lime glass or combinations thereof and more preferably soda lime glass particles.

In an even more preferred embodiment, about 25 wt-% of the particles are coated. In another more preferred embodiment about 25 wt-% of the particles are coated with a hydrophobic coating.

In yet another embodiment, 100 wt-% of glass particles have a diameter of less than 150 µm, between 90 wt-% and 100 wt-% have a diameter of less than 100 µm, between 80 wt-% and 100 wt-%, and preferably between 83 wt-% and 97 wt-%, have a diameter of less than 63 µm, between 67 wt-% and 100 wt-%, and preferably between 67 wt-% and 88 wt-%, have a diameter of less than 45 µm and between 20 wt-% and 100 wt-%, and preferably between 20 wt-% and 40 wt-%, have a diameter of less than 24 µm. The distribution can, for example, be determined by CILAS Laser diffraction.

In another embodiment, the median diameter (mass related) of the particles is in the range of about 10 µm and about 40 µm, preferably in the range of about 25 µm to about 40 µm. The median diameter can, for example, be determined by CILAS Laser diffraction.

In yet another embodiment according to the present invention, the volume specific surface area of the particles is in the range of about 0.2 to about 2 $m^2/cm^3$, and preferably is in the range of 0.4 to about 0.8 $m^2/cm^3$. For example, the volume specific surface area of the particles can be determined by the BET method.

As another embodiment, at least 90 wt-% of glass particles have a diameter in the range of about 0.5 µm and about 100 µm, preferably in the range of about 3 µm and about 80 µm. The diameter can, for example, be determined by CILAS Laser diffraction.

In a particularly preferred embodiment, the particles of the first material are beads.

In another embodiment, the whole blood filter medium comprises polymer particles. Preferably, the polymer is selected from the group consisting of polymethylmethacrylate (PMMA), polypropylene, polyetheretherketone, polyamide, polyethersulfone, polysulfone, polytetrafluoroethylen (PTFE) or combinations thereof, and preferably is PMMA. Even more preferably, 90 wt-% of the polymethylmethacrylate particles have a diameter between 5 µm and 20 µm.

In another preferred embodiment, the polymer particles of the first material are polymer beads.

In yet another embodiment, the filter medium further comprises a second material, which is located downstream of the at least first material. Preferably, the second material is composed of granulate, preferably with a diameter of more than about 150 µm, preferably more than about 250 µm and even more preferably more than about 500 µm. More preferably, the second material comprises granulate with a diameter between about 500 and about 1000 µm. The second material can be selected from the group consisting of polymer granulate, glass granulate, ceramic granulate, mineral granulate or a combination thereof. In a preferred embodiment, the granulate particles have a diameter of more than about 150 µm, and even more preferably a diameter between about 500 µm and about 1000 µm. In another preferred embodiment, the second material consists of polymer granulate, wherein the polymer is selected from the group consisting of polymethylmethacrylate (PMMA), polypropylene, polyetheretherketone, polyamide, polysulfone, polyethersulfone, polytetrafluoroethylen (PTFE), and combinations thereof, and is preferably polypropylene.

In yet another embodiment, the filter bed is compressed. The compressed filter bed may consist of first material particles only. In yet another preferred embodiment, the filter bed may also additionally comprise a second material of granulate downstream of the at least first material.

In yet another preferred embodiment, the filter further comprises a membrane located downstream of the at least first and/or second material. Preferably the membrane is hydrophilic. Preferably, the membrane is a very low protein binding membrane with low extractables. In one embodiment, the membrane is a polyethersulfone (PES) membrane. In a preferred embodiment the PES membrane has a pore size of about 0.6 to about 1.0 μm and preferably is about 0.8 μm. The thickness of the membrane is typically between about 100 and about 150 μm.

In another embodiment, the filter medium further comprises a mesh located downstream of the first and/or (if present) second material downstream of the membrane. Preferably, the mesh is a polymeric woven mesh. A mesh with a hydrophobic surface with a pore size ensuring permeability to whole blood, blood plasma or serum is preferred. Even more preferably, the mesh provides a mesh opening of between about 250 μm and about 350 μm.

In a preferred embodiment, the mesh is a woven mesh of polyester fibers with a mesh opening of about 250 to 300 μm and an open area of 44% that provides a mesh count of 23/cm, a wire diameter of 145 μm, a weight of 110 g/m² and a thickness of 255 μm, wherein the mesh is coated with a hydrophobic coating.

In another preferred embodiment, the mesh is a woven uncoated mesh of hydrophobic fibers.

In yet another preferred embodiment, the filter medium further comprises a fiber filter layer a foam or a sponge or a combination thereof, upstream of the first material particles wherein:
  a. the fiber filter layer comprises one or more layers of woven or non-woven polymer fibers and preferably, the polymer fibers are selected from the group consisting of polyester, polypropylene, polyethylene terephthalate (PET) or a combination thereof; and is preferably a layer of non-woven polypropylene fibers, a woven mesh PET fibers or a woven mesh of polyester fibers; and
  b. the sponge comprises a water-resistant and non-swelling sponge or foam.

In a preferred embodiment, the woven PET mesh upstream of the first material particles has a mesh opening of about 51 μm, an open area of about 33%, a wire diameter of 38 μm, a weight of 30 g/m² and a thickness of 60 μm.

In yet another embodiment, the nonwoven polypropylene fiber filter layer upstream of the first material of particles forms multiple layers with varying fiber diameter. Preferably, the fiber filter layer has a weight of 429 g/m² and a mean flow pore size of 9 μm.

In another embodiment, the woven polyester fiber filter layer upstream of the first material particles has a mesh opening of 285 μm, a weight of 110 g/m² and a thickness of 255 μm.

In yet another embodiment, the sponge upstream of the first material particles is hydrophobic and non-swelling.

In another embodiment, the sponge upstream of the first material particles is a with a thickness in the range of about 0.5 mm to about 10 mm and preferably is about 7 mm.

In yet another embodiment, the sponge located upstream of the first material particles provides a pore number density in the range of about 2 pores/mm to about 4 pores/mm.

In yet another embodiment, the sponge located upstream of the first material particles is a polyurethane sponge.

In yet another preferred embodiment, the filter medium comprises:

(aa) a filter fiber layer, a foam or a sponge or a combination thereof located upstream of the at least first material,
(bb) a first material and optionally comprising a second material located downstream of the at least first material;
(cc) a sponge located downstream of the second material which can be removed from the filter and from which the filtrate can be isolated.

In yet another preferred embodiment, the filter medium comprises:
(aa) a filter fiber layer, a foam or a sponge or a combination thereof located upstream of the at least first material,
(bb) a first material and optionally comprising a second material located downstream of the at least first material;
(cc) a mesh with a pore size ensuring permeability to blood plasma and serum and whole blood located downstream of the at least first and/or second material.

In a particularly preferred embodiment, the filter medium comprises:
(aa) a filter fiber layer, a foam or a sponge or a combination thereof located upstream of the at least first material,
(bb) a first material and optionally comprising a second material located downstream of the at least first material;
(cc) a membrane with a pore size ensuring permeability to blood plasma and serum located downstream of the at least first and/or second material.

In another particularly preferred embodiment, the filter medium comprises
  (aa) the at least first material, and optionally a second material,
  (bb) a membrane located downstream of the at least first material or, if present, the second material, and
  (cc) a mesh located downstream of the membrane,
  (dd) a fiber filter layer, a foam or a sponge or a combination thereof located upstream of the at least first material;
  wherein the at least the first material is compressed between the mesh downstream and the fiber filter layer, foam or sponge or combination thereof.

In another preferred embodiment, the sample volume is between about 0.01 ml and about 10 ml, preferably between about 0.1 ml and about 5 ml and even more preferably between about 0.5 ml and about 2 ml.

In yet another embodiment, the filter comprises between about 10 mg and about 5.0 g of the at least first material, preferably between about 1.0 g and about 4.0 g of the first material and even more preferably between about 1 g and about 2.5 g of the first material.

In a further embodiment, the whole blood is diluted with isotonic sodium chloride solution. Preferably, the whole blood sample is diluted with isotonic sodium chloride solution, in a ratio of from about 0.5:1.0 to about 1.0:5.0, preferably in a ratio of from about 1.0:1.0 to about 1.0:4.0.

In a preferred embodiment the whole blood of the sample is stabilized with an anti-coagulation agent selected from the group consisting of EDTA, citrate, heparin and combinations thereof.

In another preferred embodiment, the whole blood of the sample is pre-treated with a cell agglomeration agent, such as lectin.

In another embodiment of the process, the sample of whole blood is depleted of blood cells by a different method, after which there are still blood cells present in the sample, e.g. by an incomplete separation of the blood cells from serum/plasma by centrifugation or by sedimentation.

It should be emphasized that the process according to the invention as defined above is particularly advantageous for separation processes such as the separation of blood plasma/ serum from a whole blood sample, if it is used by manually operating it because, in contrast to the use of a centrifuge, the process is possible without electricity and less time consuming than a process involving a centrifuge. The process of the present invention may be performed at the place of the withdrawal of the whole blood. Therefore, the process of the present invention may be used in emergency cases, where a fast plasma/serum sample may be required for analysis, and for Point-of-Care testing as well.

The whole blood filter media and blood filtration processes according to the present invention may also be used as a solid-liquid separation in other fields, e.g. in veterinary medicine, food technology, environmental sciences, and in scientific laboratories in general. Further, the process according to the present invention may also be applied to the separation of cells from samples of other body fluids that may contain diagnostic markers, for example cerebrospinal fluid, urine, or saliva.

Example 1: Blood Plasma Separation Using Different Filter Materials

Fresh human whole blood samples were pre-treated with heparin to prevent coagulation. All testing volumes were between about 1 ml and about 3 ml for each filtration experiment. All samples were shaken to mix the settled blood cells with the blood plasma immediately before the beginning of the filtration process.

a) Composition of Filter

The filters comprised between about 1 g to about 3 g filter medium. The filter medium comprised either glass beads or polymer beads. The experiments were performed using different filters, namely Filter 1, Filter 2, Filter 3 and Filter 4.

In Filter 1 and Filter 2, the glass beads of the bulk filter medium comprised uncoated soda lime glass beads Spheriglass® solid glass microspheres grade 2000 from Potters Industries LLC. According to laser particle analysis exceeding BS 6088 requirements, 100 wt-% of glass beads have a diameter of less than 150 µm, 99.8-100 wt-% have a size of less than 100 µm, 83-97 wt-% have a diameter of less than 63 µm, 67-88 wt-% have a diameter of less than 45 µm and 20-40 wt-% have a diameter of less than 24 µm. Further, 90 wt-% of the glass beads had a diameter in the range of 3 µm to 80 µm and a median diameter between 27 and 36 µm. Downstream of the beads was a PES hydrophilic membrane by Sterlitech with a pore size of 0.8 µm and the filter medium was further stabilized downstream by a woven mesh of polyester fibers called Hyphobe 285/44 from Saatitech, which provides a hydrophobic coated surface with a mesh opening of 285 µm, as a mesh. Furthermore, Filter 1 provided a woven mesh made of PETEX® PET material by Sefar with a mesh opening of 51 µm which was located upstream of the first material.

Filter 3 provided clear poly(methyl methacrylate) microspheres from Cospheric as first material beads. The beads provided a sphericity of more than 0.99 and more than 90 wt-% have a diameter in the range of 5 µm to 20 µm. Furthermore, Filter 3 provided downstream of the first material a PES hydrophilic membrane by Sterlitech with a pore size of 0.8 µm and the filter was further stabilized downstream by a fiberwoven mesh of polyester fibers called Hyphobe 285/44 from Saatitech, which provides a hydrophobic coated surface and a mesh opening of 285 µm. Filter 3 provided a nonwoven mesh of meltblown polypropylene fibers of LyPore MB CL9005 upstream of the first material beads.

Filter 4 provided a filter medium that consisted of a bed of uncoated Spheriglass® solid glass microspheres grade 2000 and downstream a second material of REIDT glass particles MG-20/30 with a diameter between 500 µm and 1000 µm. Downstream of the first material, Filter 4 contained a PES hydrophilic membrane and the Hyphobe mesh as described above. Upstream of the bulk filter medium Filter 4 contained a filter fiber layer of LyPore MB CL9005 as described above.

b) Whole Blood Filtration

A syringe was filled with human whole blood and tapped on the upper inlet of the filter and the plunger was lowered slowly and steadily to fill the different filters with the blood until the surface of the filter was fully wetted. By this method, the filter was typically charged with about 1-2 ml of whole blood. Further, a homogenous wetting of the upstream surface of the filter was enhanced by carefully shaking the filter module. The filter was kept vertically during the process. After injection of the sufficient amount of whole blood, the syringe was removed and an empty syringe was tapped for air pumping to generate a pressure and to press the fluid through the filter medium. Initially no pressure was generated and the separation between blood cells and plasma, possibly by capillary forces, could be observed. Pressure was induced as soon as the plasma front reached the membrane, eluting the filtrate into an Eppendorf tube.

The process using Filter 1 yielded one clear yellow colored plasma droplet. As soon as the red front reached the membrane, the membrane turned red and plugged and released a red fluid of hemolyzed plasma.

In the process using Filter 2, a clear separation after injection of the whole blood was observed inside the filter into a first frontier of wetted yellow-orange plasma and a second frontier with a dark red color. After the generation of pressure as soon as the plasma frontier arrived at the bottom of the filter bed, the first obtained filtrate droplets were clear and yellow. The initial filtrate was cell-free according to a cell-counting measurement with a Coulter Counter. After further pressure generation, the filtrate turned red but was still clean and probably cell free, probably containing hemolyzed plasma.

The process using Filter 3 also resulted in a separation of a red blood front and a yellow plasma front inside the filter bed. 100-200 µl of plasma filtrate were obtained after application of pressure as the plasma front reached the membrane.

In the process using Filter 4 it was observed that the wetting of the whole blood filter with plasma occurred slightly faster than in similar whole blood filters without a second material.

Example 2: Analysis of Diagnostic Marker after Blood Plasma Filtration Process

In order to obtain adequate diagnostic marker results, the whole blood filtration was performed in a housing of medically applicable polypropylene. The bulk filter consisted of uncoated Spheriglass® solid glass microspheres grade 2000 and downstream was a PES membrane and a Hyphobe mesh as described above. Additionally, a PES membrane and a Hyphobe mesh were located upstream of the bed of glass spheres. To focus on possible deviations of plasma diagnostic markers due to interactions between the plasma and the bulk filter medium, pre-centrifuged plasma samples were used in the filtration process.

A syringe was filled with the preseparated and pre-centrifuged plasma sample and tapped on the upper inlet of the filter and the plunger was lowered slowly and steadily to fill the filter with the plasma until the surface of the filter was fully wetted. Further, a homogenous wetting of the upstream surface of the filter was enhanced by carefully shaking the filter module. The filter was kept vertically during the process. After injection of the sufficient amount of sample, the syringe was removed and an empty syringe was tapped for air pumping to generate a pressure and to press the fluid through the filter medium, eluting the filtrate into an Eppendorf tube followed by a plasma analysis using the "Dimension" analysis device from Siemens for the analysis of a representative set of diagnostic markers. The experiment was independently repeated three times.

The analytes of diagnostic markers and the deviations of the filtered plasma sample compared to the reference plasma sample, which had no contact with the filter, are shown in the following table 1. In light of the relatively high volume of bulk filter material of 4.5 g that was used for the filtration, the deviations are quiet low and a deviation up to 20% only occurred for a few analytes like potassium, GOT and IgG. One critical analyte, namely sodium, was elevated after the filter medium passage, which is an indicator that the filter medium comprised impurities which were flushed out with the plasma.

| | Diagnostic marker | Change sample 1 [%] | Change sample 2 [%] | Change sample 3 [%] |
|---|---|---|---|---|
| Electrolytes | K | −19.0 | −11.4 | −8.9 |
| | Na | 30.2 | 16.9 | 15.6 |
| Lipometabolism | Triglyceride | −6.1 | −11.1 | −1.8 |
| | Cholesterol | −6.4 | 3.1 | 1.3 |
| | HDL-Cholesterol | −4.2 | 5.6 | 2.4 |
| | LDL-Cholesterol | −6.8 | 5.7 | 1.9 |
| Infection marker | CRP | −2.8 | −3.8 | 5.0 |
| Enzymes | GOT/AST | −10.3 | 6.3 | 0.0 |
| | Lipase | −4.4 | 4.2 | 1.3 |
| Substrates | Albumin | 0.0 | 0.0 | 0.0 |
| | Bilirubin total | 0.0 | 0.0 | 0.0 |
| | Glucose | 2.2 | 0.7 | 1.8 |
| | Creatinine | 0.0 | 0.0 | 7.7 |
| Proteins | IgG | −10.9 | −14.9 | −5.6 |
| | Ferritine | 0.2 | 0.9 | 1.8 |
| Hormones | TSH basal | −6.7 | −1.3 | 1.0 |

The invention claimed is:

1. A process for filtering whole blood for separating plasma/serum from blood cells using a filter that comprises a filter medium comprising:
   a first material comprising glass beads arranged in a filter bed, the glass beads having a sphericity higher than 0.7;
   a sponge filter layer arranged at an upstream side of the filter bed, the sponge filter layer configured to distribute the whole blood over the upstream side of the filter bed, the sponge filter layer comprising a porous fiber, foam or sponge material which can soak up whole blood fluids and distribute the whole blood fluids within the sponge filter layer;
   a second material arranged on a downstream side of the filter bed, the second material comprising at least one of a membrane or a mesh;
   the process comprising the steps of
     applying a whole blood sample onto an upstream side of the sponge filter layer;
     distributing the whole blood sample through the sponge filter layer onto an upstream side of the glass beads of the filter bed;
     filtering the whole blood sample though the filter bed such that blood cells remain in the filter bed and plasma/serum exits through the second material at the downstream side of the filter bed;
   wherein the applying step includes
     applying a positive or a negative pressure to the whole blood sample at the upstream side of the sponge filter layer to urge the whole blood sample through the filter medium;
   separating the blood cells from the plasma/serum; and
   collecting the plasma/serum on a downstream side of the second material.

2. Process of claim 1, wherein in the process step of applying a whole blood sample, the whole blood sample is homogenously distributed onto the upstream side of the sponge filter layer.

3. The process of claim 1, wherein the glass beads are uncoated.

4. The process of claim 1, wherein the glass beads are coated with a hydrophobic coating.

5. The process of claim 1, wherein between 0 wt-% and 75 wt-% of glass beads are coated with a hydrophobic coating.

6. The process of claim 1, wherein 100 wt-% of glass beads have a diameter of less than 150 μm, between 90 wt-% and 100 wt-% have a diameter of less than 100 μm, between 80 wt-% and 100 wt-% have a diameter of less than 63 μm, between 67 wt-% and 100 wt-% have a diameter of less than 45 μm, or between 20 wt-% and 100 wt-% have a diameter of less than 24 μm.

7. The process of claim 1, wherein at least 90 wt-% of glass beads have a diameter in the range of about 0.5 μm and about 100 μm.

8. The process of claim 1, wherein the bed is a volume of glass beads in the range between 10 microliter to 10 ml.

9. The process of claim 8, wherein the glass beads in the bed is compressed between the sponge filter layer and the second material.

10. The process of claim 1, wherein the second material further comprises material selected from the group consisting of:
   a. glass granulate with a diameter of more than 150 μm with a diameter between 500 μm and 1000 μm,
   b. polymer granulate with a diameter of more than 150 μm wherein the polymer granulate includes polypropylene and further includes a polymer granulate selected from the group consisting of polymethylmethacrylate (PMMA), polyetheretherketone, polyamide, polysulfone, polyethersulfone, polytetrafluoroethylene (PTFE), and combinations thereof
   c. ceramic granulate, and
   d. combinations thereof.

11. The process of claim 10, wherein the filter medium further comprises a membrane located downstream of the first and/or second material, wherein the membrane is hydrophilic.

12. The process of claim 1, wherein in the step of applying a positive or negative pressure, the pressure is applied either:
   aa) immediately after the application of the whole blood to the filter medium until the whole blood is in contact with the first material and/or
   bb) after the filter bed is fully wetted.

13. The process according to claim 1, wherein the filter medium further comprises downstream a polymeric woven mesh with a hydrophobic surface.

14. The process of claim 13, wherein the mesh provides a pore size ensuring permeability to whole blood.

15. Process of claim 1, wherein the sponge filter layer comprises a water-resistant and non-swelling sponge or foam.

16. Process of claim 1, wherein the whole blood sample has a volume between 0.01 ml and 10 ml.

17. Process according to claim 1, wherein before step of applying a whole blood sample, the whole blood sample is pre-treated in at least one of the following steps of:
  a) dilution with isotonic sodium chloride solution with a 0.9% sodium chloride solution (w:v), in a ratio of from 0.5:1 to 1:5;
  b) treatment with an anti-coagulation agent selected from the group consisting of EDTA, citrate, heparin and combinations thereof;
  c) treatment with a cell agglomeration agent; and
  d) incomplete depletion of blood cells.

18. A process for filtering whole blood for separating plasma/serum from blood cells using a filter that comprises a filter medium comprising:
  a first material comprising beads arranged in a filter bed, the filter bed having an upstream side and a downstream side oppositely arranged, the beads of a material selected from the set consisting of: polymers, ceramics and minerals; the beads having a sphericity higher than 0.7;
  a sponge filter layer arranged at an upstream side of the filter bed, the sponge filter layer configured to distribute the whole blood over the upstream side of the filter bed, the sponge filter layer comprising a porous fiber, foam or sponge material which can soak up whole blood fluids and distribute the whole blood fluids within the sponge filter layer;
  a second material arranged on a downstream side of the filter bed, the second material comprising at least one of a membrane or a mesh;
  the process comprising the steps of
    applying a whole blood sample onto an upstream side of the sponge filter layer;
    distributing the whole blood sample through the sponge filter layer onto an upstream side of the beads of the filter bed;
    filtering the whole blood sample though the filter bed such that blood cells remain in the filter bed and plasma/serum exits through the second material at the downstream side of the filter bed;
  wherein the applying step includes
    applying a positive or a negative pressure to the whole blood sample at the upstream side of the sponge filter layer to urge the whole blood sample through the filter medium;
  separating the blood cells from the plasma/serum; and
  collecting the plasma/serum on a downstream side of the second material.

19. The process of claim 18, wherein
  the bed is a volume of beads in the range between 10 microliter to 10 ml,
  wherein the beads in the bed is compressed between the sponge filter layer and the second material.

20. The process of claim 18, wherein in the step of applying a positive or negative pressure, the pressure is applied either:
  aa) immediately after the application of the whole blood to the filter medium until the whole blood is in contact with the first material and/or
  bb) after the filter bed is fully wetted.

21. The process according to claim 18, wherein the filter medium further comprises downstream polymeric woven mesh with a hydrophobic surface.

22. The process of claim 18, wherein a mass related median diameter of the beads is in the range of about 10 μm and about 40 μm.

23. The process of claim 22, wherein the volume specific surface area of the beads is in the range of about 0.2 to about 2 $m^2/cm^3$.

24. The process of claim 18, wherein the polymer beads comprise polymethylmethacrylate (PMMA) polymer particles.

25. The process of claim 24, wherein the polymer beads further include polymer particles selected from the group consisting of polypropylene, polyetheretherketone, polyamide, polysulfone, polyethersulfone, polytetrafluoroethylene (PTFE), and combinations thereof.

26. The process of claim 24, wherein at least 90 wt-% of polymer beads have a diameter in the range of about 5 μm to about 20 μm.

* * * * *